(12) United States Patent
Erndt-Marino et al.

(10) Patent No.: US 11,406,612 B2
(45) Date of Patent: Aug. 9, 2022

(54) METHOD OF TREATMENT VIA INTRA-ARTICULAR APPLICATION OF POTASSIUM

(71) Applicant: Rensselaer Polytechnic Institute, Troy, NY (US)

(72) Inventors: Joshua Erndt-Marino, Tuckerton, NJ (US); Mariah Hahn, Ballston Lake, NY (US)

(73) Assignee: Rensselaer Polytechnic Institute, Troy, NY (US)

( * ) Notice: Subject to any disclaimer, the term of this patent is extended or adjusted under 35 U.S.C. 154(b) by 454 days.

(21) Appl. No.: 16/285,348

(22) Filed: Feb. 26, 2019

(65) Prior Publication Data

US 2019/0262295 A1     Aug. 29, 2019

Related U.S. Application Data

(60) Provisional application No. 62/808,419, filed on Feb. 21, 2019, provisional application No. 62/634,965, filed on Feb. 26, 2018.

(51) Int. Cl.
*A61K 31/194* (2006.01)
*A61K 31/191* (2006.01)
*A61K 35/12* (2015.01)

(52) U.S. Cl.
CPC .......... *A61K 31/194* (2013.01); *A61K 31/191* (2013.01); *A61K 35/12* (2013.01)

(58) Field of Classification Search
CPC combination set(s) only.
See application file for complete search history.

(56) References Cited

U.S. PATENT DOCUMENTS

2018/0344750 A1    12/2018  Kim et al.

FOREIGN PATENT DOCUMENTS

| CN | 1557290 | 12/2004 |
|----|---------|---------|
| EP | 0325199 | 10/1993 |
| KR | 20080024426 | 3/2018 |
| NZ | 578985 | 12/2011 |
| WO | 2012085609 | 6/2012 |

OTHER PUBLICATIONS

Miller James H., White John, and Norton Thomas H. "The Value of Intra-Articular Injections in Osteoarthritis of the Knee." The Journal of Bone and Joint Surgery. British vol. 1958 40-B:4, 636-643.
Desmarais MH. Value of intra-articular injections in osteo-arthritis. Ann Rheum Dis. 1952;11(4):277-281. doi:10.1136/ard.11.4.277.
Erndt-Marino, Josh & Mariah, Hahn. (2016). Membrane potential controls macrophage activation. Frontiers in Bioengineering and Biotechnology. 4. 10.3389/conf.FBIOE.2016.01.00360.

*Primary Examiner* — Heidi Reese
(74) *Attorney, Agent, or Firm* — Murtha Cullina LLP; Anthony P. Gangemi (57) ABSTRACT

Resolution of a pathological condition is promoted via the application, e.g., via injection, of a potassium osmolyte such as hyperosmolar potassium gluconate, potassium aspartate, another potassium-based salt, or combinations thereof to the condition site. The application of the potassium osmolyte increases the extracellular concentration of potassium ions, reducing the membrane potential of the cells at the condition site and including immune cell quiescence. As a result, the inflammatory response in the patient to the pathological condition is reduced or eliminated. Reducing the inflammatory response is useful in treatment of myriad conditions including arthritis, auto-immune conditions, inflammatory disorders, neurodegenerative disorders, neurodevelopmental disorders, tissue breakdown, etc.

5 Claims, 9 Drawing Sheets

METHOD OF TREATMENT VIA INTRA-ARTICULAR APPLICATION OF POTASSIUM

CROSS REFERENCE TO RELATED APPLICATION(S)

This application claims the benefit of U.S. Provisional Application Nos. 62/634,965, filed Feb. 26, 2018, and 62/808,419, filed Feb. 21, 2019, which are incorporated by reference as if disclosed herein in their entireties.

BACKGROUND

Osteoarthritis (OA) is characterized by a slow progression of cartilage degradation driven in part by a cascade of inflammatory mediators produced from an activated synovium and the cartilage itself. The tissue level changes associated with the disease are a result of the aberrant phenotypes of the cells in each tissue. In particular, chondrocytes lose their capacity to maintain a healthy cartilage extracellular matrix (ECM) as they transition from an anabolic, healthy phenotype to a catabolic, hypertrophic phenotype. Activated synovial macrophages contribute to the chondrocyte phenotype shift and subsequent cartilage degradation through the secretion of pro-inflammatory molecules. Currently, there is not a clinically proven effective disease modifying treatment which can intervene in this degradative cascade.

To prevent the joint from reaching end-stage OA, drug- or cell-based IA injections are utilized as potential disease modifying therapies to locally deliver chondroprotective, pro-regenerative factors and/or target inflammation to intervene in the OA disease cascade. Drug-based approaches, which often target specific components of the disease offer simplicity and ease of scalability to a final product, but have been met with little and/or controversial success. Cell-based IA injections capable of modulating more than one specific component of OA have demonstrated more success, although variable, in pre-clinical and early clinical trials. However, cell-based therapies suffer from several limitations, most of which are a result of the underlying complexity associated with using cells. Confounding variables such as cell type, source, and culture conditions can all influence outcome and therefore make it difficult to pinpoint the reason for success or failure across trials, hampering progress towards a safe and efficacious disease modifying therapy. In addition, these cell-based alternatives inherently face more regulatory and scalability challenges compared to drug-based approaches.

Although many researchers in OA recognize chondrocyte hypertrophy as a main component of disease, no available intra-articular treatments have been designed to slow down or reverse this process. Macrophage activation is currently targeted with antibodies for macrophage-secreted cytokines, immunomodulatory MSCs, or radionuclides which kill synovial macrophages through phagocytosis of radioactive material.

Alongside more popular and traditionally thought of biochemical cues and pathways, bioelectric signals (endogenous ion flows) have been identified as instructors of pattern formation, regeneration, and cell phenotype. Bioelectric signals are created by ion channels and pumps embedded within cell membranes to establish a cell transmembrane voltage potential and control flux of charged particles. These signals have been demonstrated to exert some level of influence over cell phenotype. Specifically, elevated levels of extracellular potassium can suppress mesenchymal stem cell differentiation into fat or bone even in the presence of the powerful chemical inducers.

SUMMARY

Some embodiments of the present disclosure are directed to a method of treating a patient including identifying inflammation of a joint of the patient and administering to the intra-articular region of the joint an amount of a therapeutic composition. In some embodiments, the therapeutic composition includes a potassium osmolyte.

In some embodiments, the present disclosure is directed to a method of promoting resolution of a pathological condition including diagnosing the patient as having a condition resulting in inflammation or tissue breakdown at a localized area of the patient's body, and administering to the localized area a therapeutic composition including one or more osmolytes to reduce membrane potential and/or change the ionic composition of cells at the localized area.

In some embodiments, the present disclosure is directed to a method of treating a patient having a pathological condition via immune cell quiescence including identifying a pathological condition at a localized area of the patient's body, and increasing extracellular concentration of potassium at the localized area to promote immune cell quiescence. In some embodiments, the pathological condition is arthritis, an auto-immune condition, inflammatory disorder, neurodegenerative disorder, neurodevelopmental disorder, tissue breakdown, or combinations thereof.

BRIEF DESCRIPTION OF THE DRAWINGS

The drawings show embodiments of the disclosed subject matter for the purpose of illustrating the invention. However, it should be understood that the present application is not limited to the precise arrangements and instrumentalities shown in the drawings, wherein.

DETAILED DESCRIPTION

Figure 1:
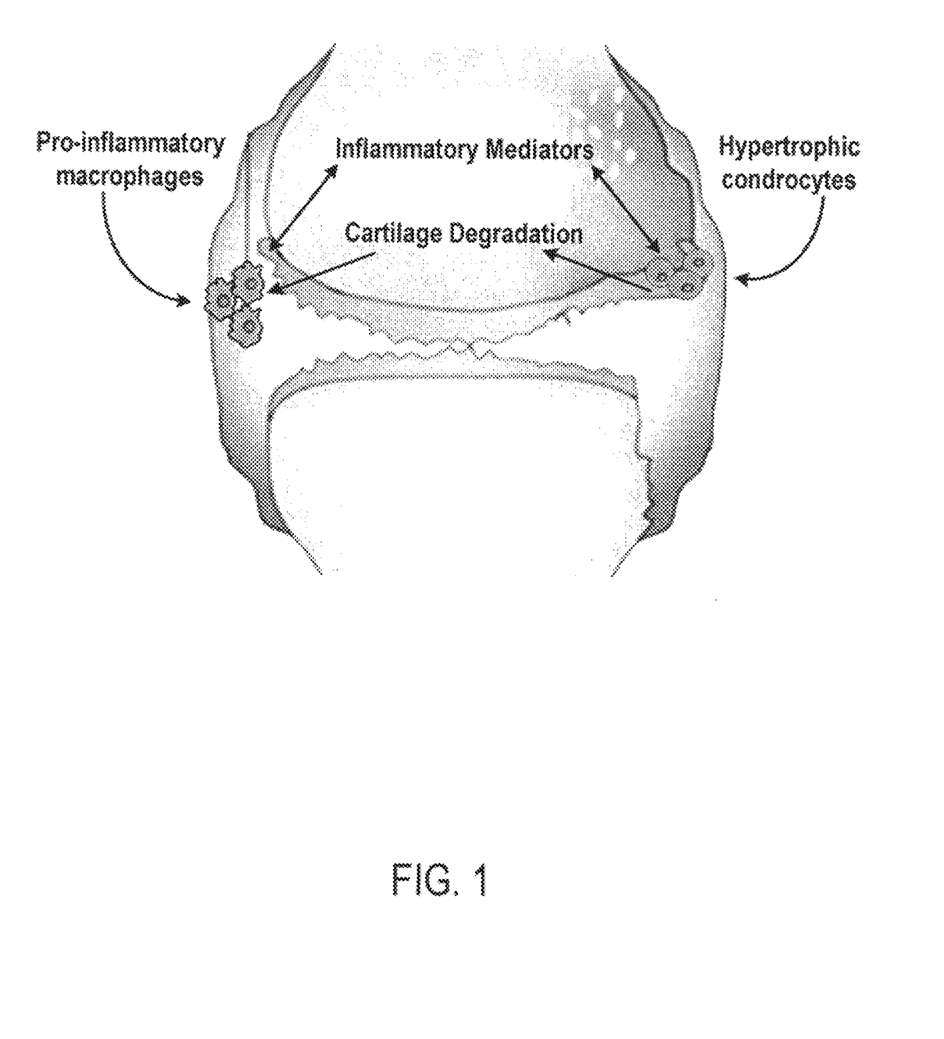
FIG. 1 is a schematic drawing depicting osteoarthritis-linked proinflammatory chondrocyte and macrophage activation.
Figure 2A:
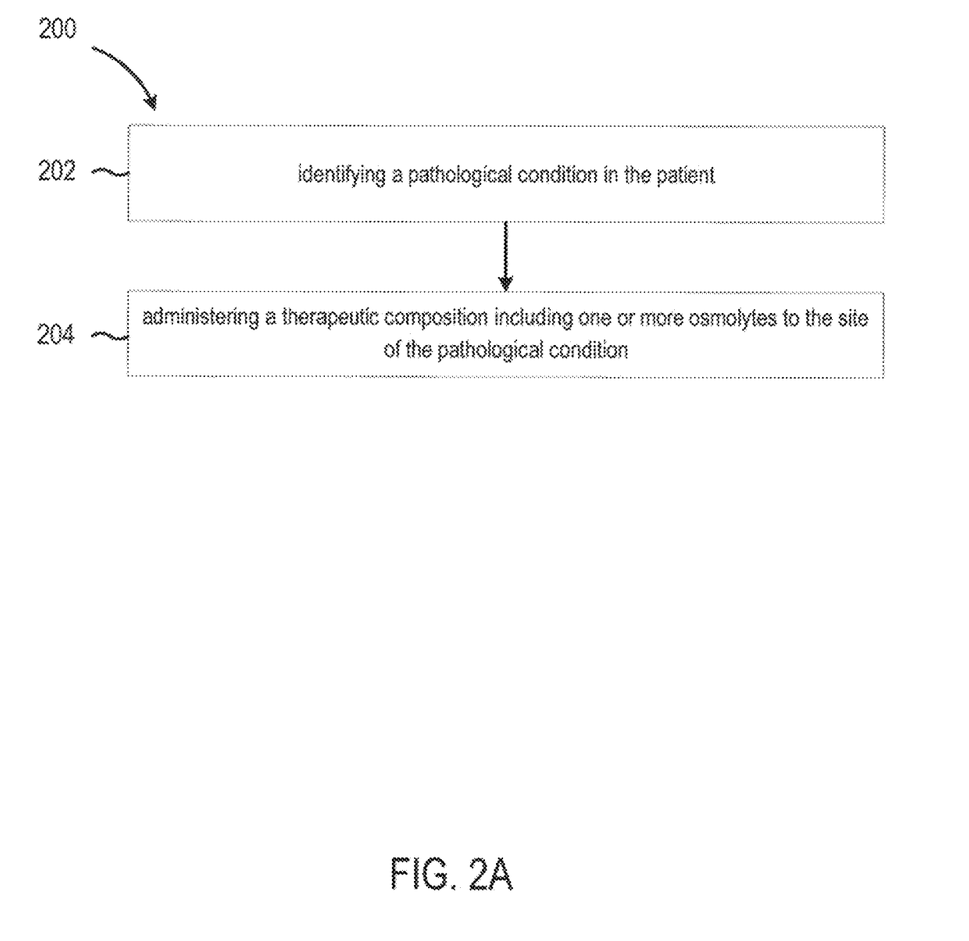
FIG. 2A is a chart of a method of promoting resolution of a pathological condition according to some embodiments of the present disclosure.

Referring now to FIG. 2A, some aspects of the disclosed subject matter include a method 200 of treating a patient including identifying, at 202, a pathological condition in the patient. In some embodiments, the pathological condition includes arthritis, an auto-immune condition, inflammatory disorder or condition, e.g., osteoarthritis, rheumatoid arthritis, surgery at or proximate to the joint, or combinations thereof, neurodegenerative disorder, neurodevelopmental disorder, tissue breakdown, or combinations thereof. At 204, a therapeutic composition including one or more osmolytes is administered to the site of the pathological condition. In some embodiments, the therapeutic composition also includes pharmaceutically acceptable adjuvants, diluents, excipients, carriers, additional medicaments, apoptotic cells, stem cells, or combinations thereof In some embodiments, the one or more osmolytes includes a potassium osmolyte. In some embodiments, the therapeutic composition is administered via injection, oral administration, topical administration, inhalation, or combinations thereof. Without wishing to be bound by theory, the application of one or more osmolytes to the site of the pathological condition increases the extracellular concentration of the associated ions, e.g., potassium ions, at the site. This increased extracellular concentration results in the limitation or decrease in resting cellular membrane potential ($V_{mem}$), particularly of localized chondrocytes and macrophages exhibiting proinflammatory phenotypes. Instead, the phenotypes revert towards more anti-inflammatory resting or proliferative phenotypes, interrupting the degenerative cascade of inflammatory mediators and limiting tissue degradation, e.g., cartilage.

In some embodiments, the concentration of osmolyte at the site of the pathological condition is made to be above about 2 mM. In some embodiments, the concentration of osmolyte at the site of the pathological condition is made to be above about 40 mM, 50 mM, 60 mM, 70 mM, 80 mM, 90 mM, or 100 mM.

Figure 2B:
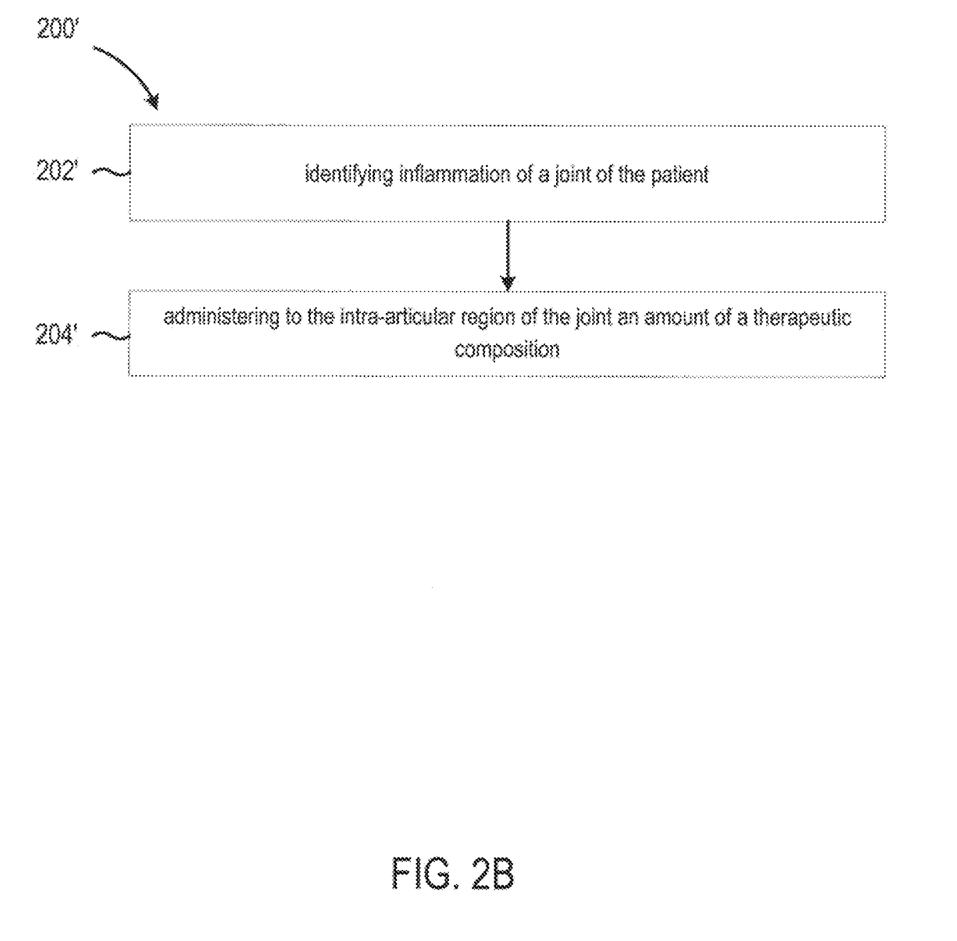
FIG. 2B is a chart of a method of promoting resolution of a pathological condition according to some embodiments of the present disclosure.

In the exemplary method 200' embodiment shown in FIG. 2B, the pathological condition identified at 202' is inflammation, e.g., inflammation of a joint of the patient. In the exemplary embodiment of joint inflammation, the therapeutic composition is administered 204' to the joint. In some embodiments, the therapeutic composition is administered to the intra-articular region of the joint. In some embodiments, the concentration of the potassium ions in the intra-articular space is made to be above about 2 mM. In some embodiments, the concentration of the potassium ions in the intra-articular space is made to be above about 40 mM, 50 mM, 60 mM, 70 mM, 80 mM, 90 mM, or 100 mM. In some embodiments, identifying step 202' includes identifying increased activation, in or proximate to the intra-articular region, of chondrocytes, macrophages, or combinations thereof In the exemplary embodiment shown in FIG. 2B, the site of the pathological condition is a joint of the patient, however the present disclosure is not limited in this regard, as the site of the pathological condition can be any area of a patient's body exhibiting a pathological condition, such as a bodily system, an individual structure within a bodily system, a specific organ, an individual structure within an organ, an extremity, individual structures within an extremity, etc.

In some embodiments, the potassium osmolyte includes any biocompatible solid, liquid, or gas including potassium ions. In some embodiments, the potassium osmolyte includes a hyperosmolar $K^+$ solution. In some embodiments, the hyperosmolar $K^+$ solution includes potassium gluconate, potassium aspartate, another potassium-based salt, or combinations thereof.

Figure 3:
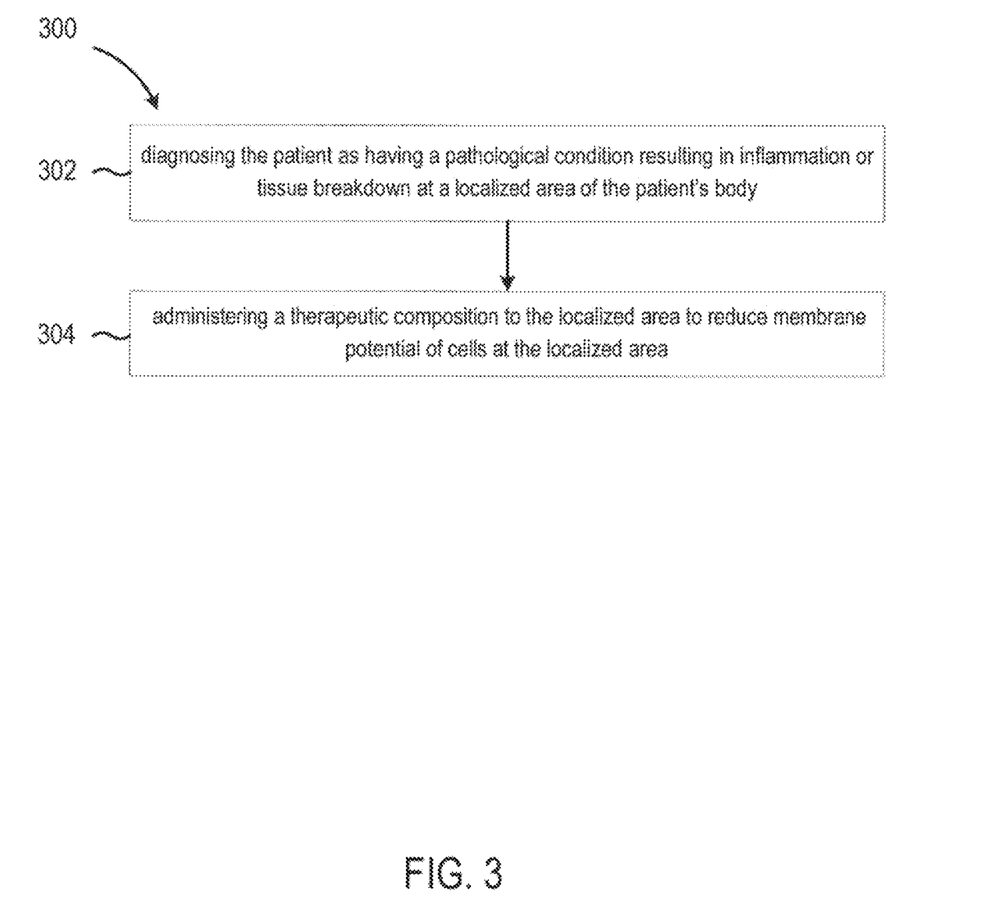
FIG. 3 is a chart of a method of promoting resolution of a pathological condition according to some embodiments of the present disclosure.

Referring now to FIG. 3, some embodiments of the present disclosure relate to a method 300 of promoting resolution of a pathological condition resulting in inflammation or tissue breakdown. In some embodiments, the pathological condition includes osteoarthritis, rheumatoid arthritis, non-healing of skin wounds, fibrosis, surgery at or proximate to the localized area, etc., or combinations thereof. At 302, the patient is diagnosed as having a condition at a localized area of the patient's body. At 304, a therapeutic composition is administered to the localized area to reduce membrane potential of cells at the localized area. As discussed above, in some embodiments, the therapeutic composition includes one or more osmolytes. In some embodiments, the therapeutic composition includes a hyperosmolar $K^+$ solution. In some embodiments, the hyperosmolar $K^+$ solution includes potassium gluconate, potassium aspartate, another potassium-based salt, or combinations thereof In some embodiments, the concentration of the potassium ions in the localized area is made to be above about 2 mM. In some embodiments, the concentration of the potassium ions in the localized area is made to be above about 40 mM, 50 mM, 60 mM, 70 mM, 80 mM, 90 mM, or 100 mM. As discussed above, in some embodiments, the localized area is an intra-articular region of the joint, however the present disclosure is not limited in this regard, as the localized area can be any area of a patient's body exhibiting the pathological condition, such as a bodily system, an individual structure within a bodily system, a specific organ, an individual structure within an organ, an extremity, individual structures within an extremity, etc.

Figure 4A:
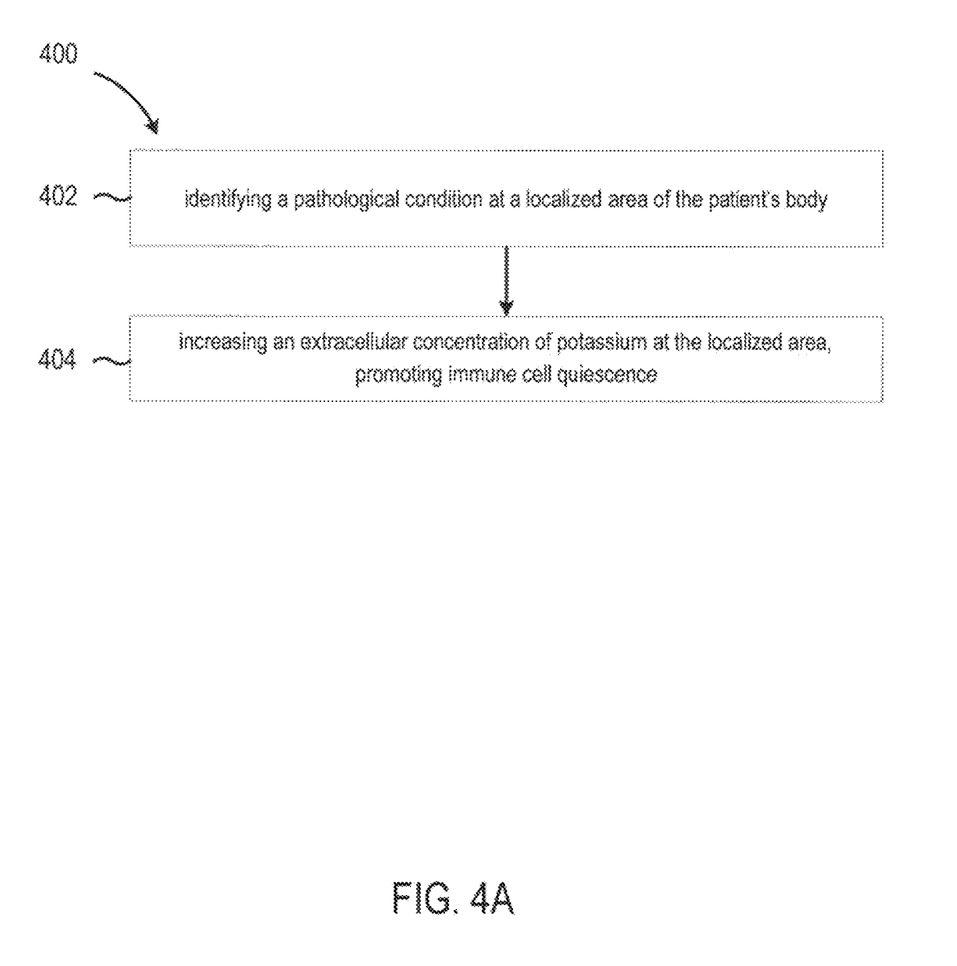
FIG. 4A is a chart of a method of promoting resolution of a pathological condition according to some embodiments of the present disclosure.
Figure 4B:
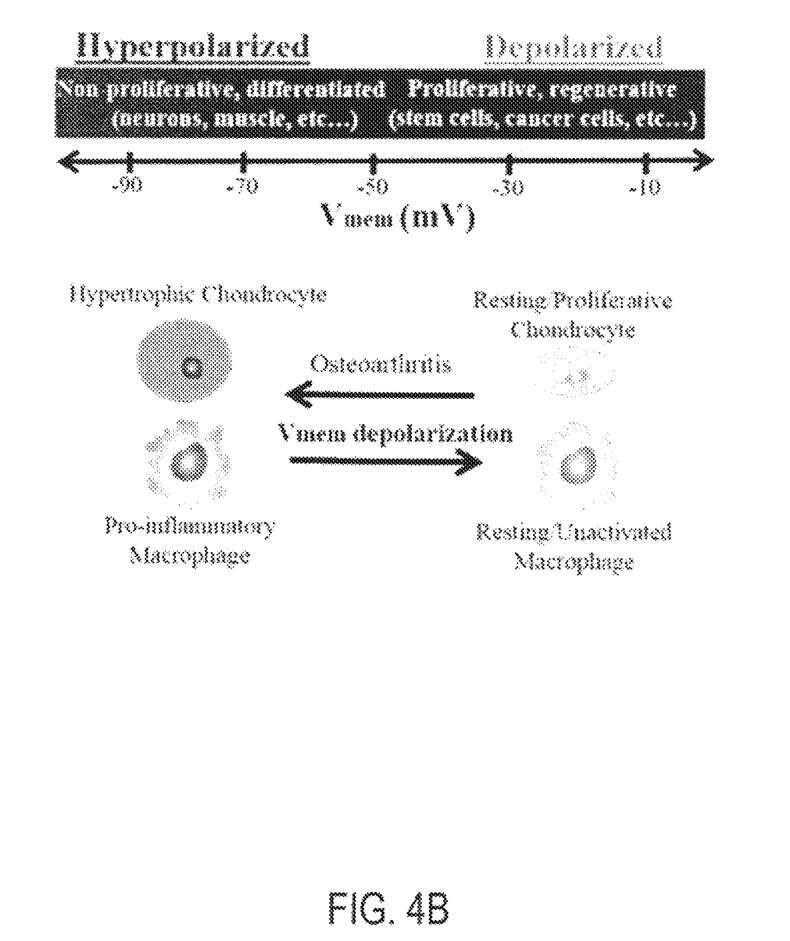
FIG. 4B is a schematic representation of a method of promoting resolution of a pathological condition according to some embodiments of the present disclosure.

Referring now to FIGS. 4A and 4B, some embodiments of the present disclosure relate to a method 400 effective in treating a patient having a pathological condition via immune cell quiescence. As discussed above, in some embodiments, the pathological condition includes arthritis, an auto-immune condition, inflammatory disorder, neurodegenerative disorder, neurodevelopmental disorder, tissue breakdown, etc., or combinations thereof. At 402, a pathological condition at a localized area of the patient's body is identified. At 404, an extracellular concentration of potassium is increased at the localized area, promoting immune cell quiescence. In some embodiments, the extracellular concentration of potassium is increased to above about 2 mM. In some embodiments, the extracellular concentration of potassium is increased to above about 40 mM, 50 mM, 60 mM, 70 mM, 80 mM, 90 mM, or 100 mM.

Figure 5A:
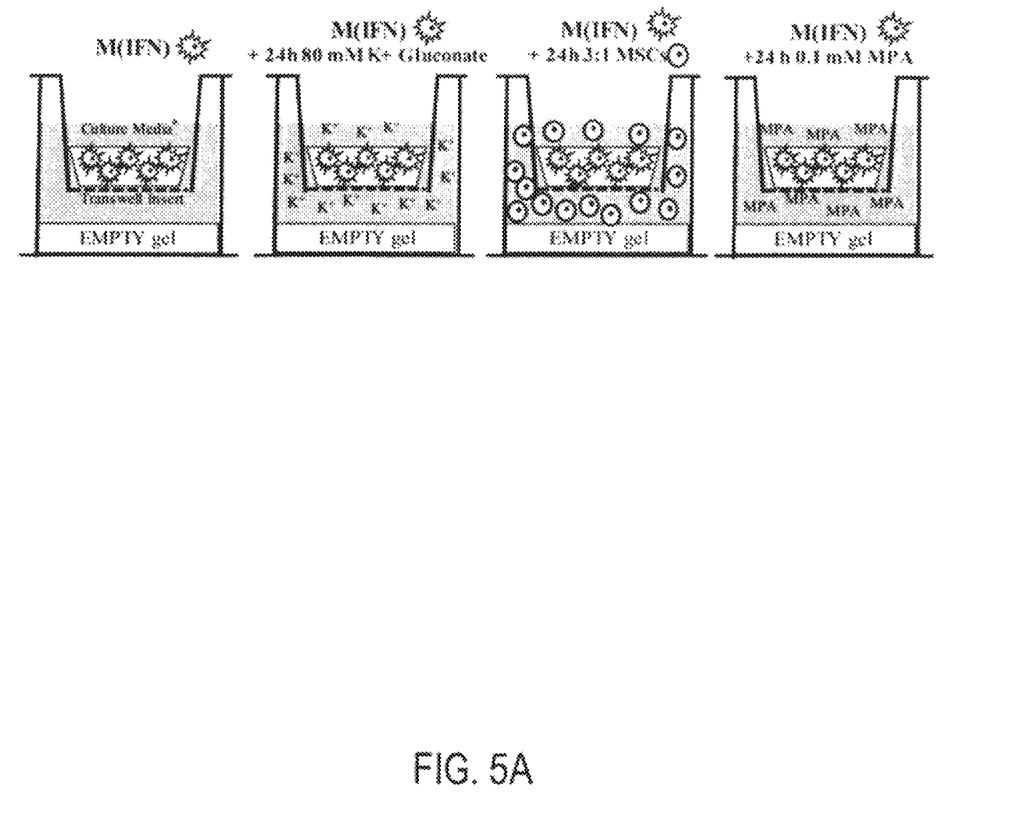
FIG. 5A portrays an experimental design mimicking an intra-articular injection of a therapeutic compound promoting resolution of a pathological condition according to some embodiments of the present disclosure.

Referring now to FIG. 5A, an in vitro experiment was designed to mimic an intra-articular injection of potassium osmolytes consistent with the embodiments described above. Poly(ethylene glycol) diacrylate hydrogels encapsulated with proinflammatory interferon-gamma (IFN)-stimulated macrophages (M(IFN)s) were prepared. M(IFN)s were cultured for 5 days in the continued presence of IFN, with 80 mM K+ applied only during the first day and then removed. Other IA injection formulations—human mesenchymal stem cells (MSCs) and methylprednisolone acetate (MPA)—were also included to gain a sense of efficacy and benchmark against current OA treatments.

Poly(ethylene glycol) diacrylate (PEGDA) was synthesized from PEG-diol (6 kDa; Sigma Aldrich) at ~99% acrylation. $NH_2$-Arg-Gly-Asp-Ser-COOH (RGDS; American Peptide Company) was reacted with 3.4 kDa acryoyl-PEG-succinimidyl valerate (ACRLPEG-NHS; Laysan Bio) at a 1:3 molar ratio for 2 h in 50 mM sodium bicarbonate buffer (pH 8.5). RGDS was included to facilitate cell attachment within the PEGDA network. The product (ACRL-PEG-RGDS) was purified by dialysis, lyophilized, and stored at −80° C. until further use.

The PEGDA hydrogel (~50 kPa stiffness) was provided at the bottom of the culture well to create a surface that more closely matches the stiffness of articular cartilage (aggregate modulus ~500 kPa) than traditional plastic 2D surfaces (~$1×10^6$ kPa). MSC behavior is known to respond to substrate stiffness. Assessments for treatment efficacy included cell lysate levels of several proinflammatory markers, anti-inflammatory markers, and the ratio between anti/proinflammatory profiles.

Raw 264.7 murine macrophages (a cell line) were thawed and expanded in regular growth medium: high-glucose Dulbecco's modified Eagle's medium (DMEM; Corning) supplemented with 10% fetal bovine serum (FBS; Hyclone, Atlanta Biologicals, Inc.). Primary human OACs (Cell Applications, Inc.) were expanded in chondrogenic growth media for four passages, transitioned into regular growth medium for 1 passage, and utilized at passage 5. The OAC donor at this passage has been previously demonstrated to respond to activated Raw 264.7 macrophages in a manner consistent with early OA and exhibits increased production of matrix metalloproteinases (MMPs) and proinflammatory cytokines relative to chondrocytes isolated from a patient without OA.

Bone marrow-derived hMSCs were obtained as passage 1 in a cryovial from Texas A&M Institute for Regenerative Medicine. Cells were thawed and expanded in Minimum Essential Medium a (MEMa; Gibco) supplemented with 16.5% FBS (Atlanta Biologicals) and utilized at passage 4. These cells have been confirmed by Texas A&M to be $CD44^+$, $CD105^+$, $CD29^+$, $CD166^+$, $CD14^-$, $CD34^-$, and $CD45^-$ and to undergo adipogenic, chondrogenic, or osteogenic differentiation under inductive culture conditions.

Aliquots (200 mL; $1×10^6$ cells per construct) of the cell/polymer suspension were dispensed into the wells of a 48-well plate (Corning) and cured by exposure to long-wave UV light (~10 $mW/cm^2$) for 6 min. After 24 h of equilibration to the new 3D environment and activation with 75 ng/mL interferon-gamma (IFN; R&D Systems), macrophage discs were placed in culture with or without IFN, K+ gluconate (Sigma), and methylprednisolone acetate (MPA; Fisher Scientific). At culture end points, the hydrogels were washed in DPBS for 5-10 min, harvested by flash-freezing in liquid nitrogen, and stored at −80° C. until further analysis.

Figure 5B:
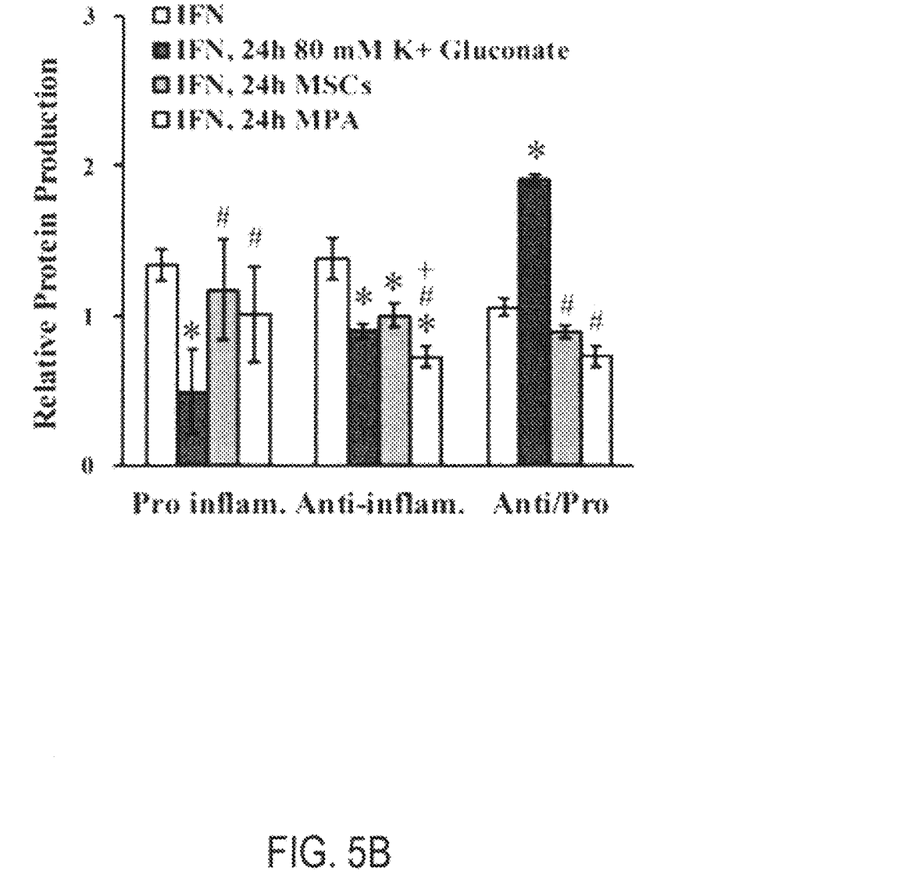
FIG. 5B portrays relative protein production after treatments with a therapeutic compound promoting resolution of a pathological condition according to some embodiments of the present disclosure.
Figure 5C:
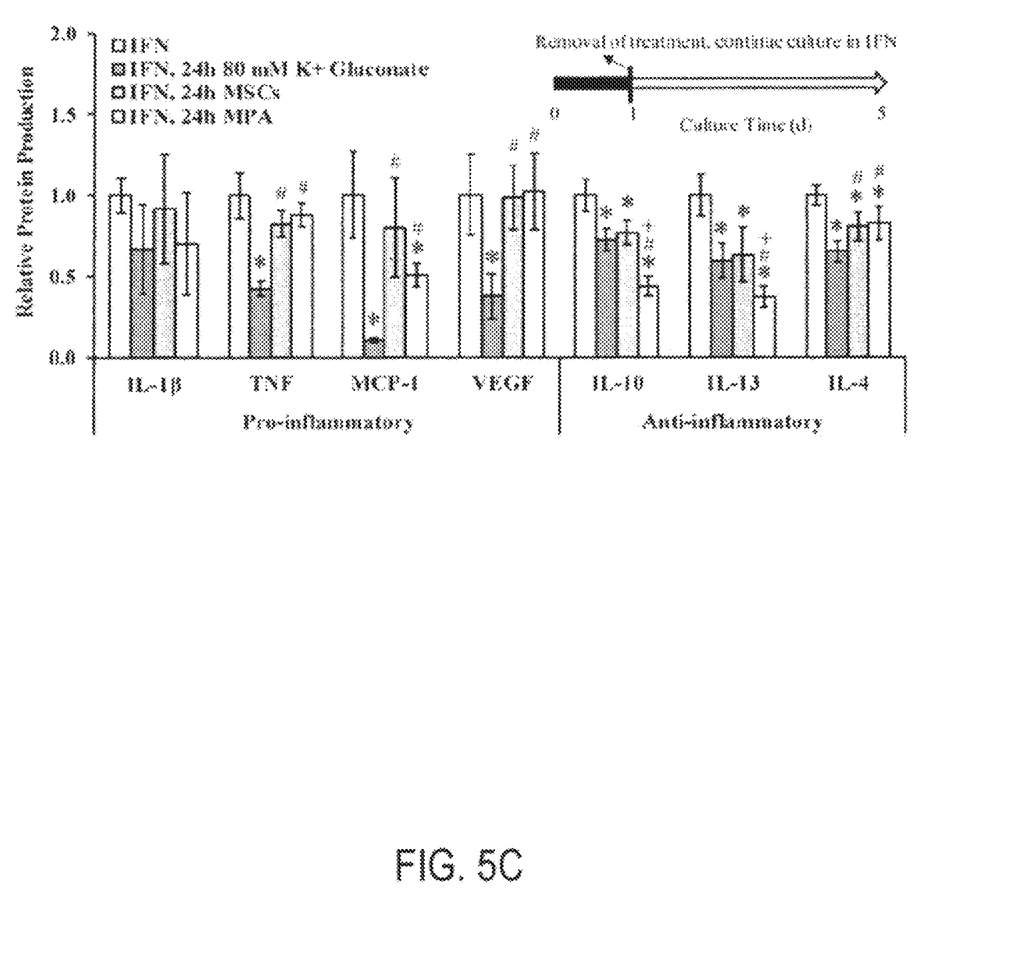
FIG. 5C portrays relative protein production after treatments with a therapeutic compound promoting resolution of a pathological condition according to some embodiments of the present disclosure.

Referring now to FIGS. 5B and 5C, relative protein production of proinflammatory and anti-inflammatory molecules and the ratio between anti/proinflammatory profiles in Raw 264.7 macrophages were determined after 5 days in culture. "*" denotes a significant difference relative to IFN controls. "#" denotes a significant difference relative to 24-h 80 mM $K^+$ gluconate. "+" denotes a significant difference relative to 24-h MSCs. In contrast to MSCs and MPA, treatment with 80 mM $K^+$ gluconate significantly enhanced the anti/proinflammatory cytokine ratio. The extended benefit from a short-term $K^+$ treatment was also noted for IL-8, MCP-1, and MMP-13 production in OACs. From an OA disease perspective, the overall decreased levels of cytokines, the enhanced ratio of anti/proinflammatory cytokines, and the reduced production of MMP-13 noted herein would seem desirable for a potential disease-modifying treatment and supports further development of K+-based solutions.

From a mechanistic perspective, suppression of M(IFN)s in addition to the shift in anti/proinflammatory ratio would suggest that 80 mM K+ gluconate drives macrophage polarization toward an anti-inflammatory/proresolving phenotype. This is consistent with K+ treatment enhancing the generation of $Foxp3^+$ Treg cells, reducing T cell effector function, and inflammatory protein production in OACs. As the extracellular $K^+$ concentration is elevated, ~40 mM in necrotic cancerous tumors, this may help explain findings of the tumor-associated macrophage phenotype. Interestingly, the anti/proinflammatory profile was not significantly different between 40 and 80-mM treatments.

Methods and systems of the present disclosure advantageously suppress condition-associated proinflammatory responses in the patient, making the therapeutic compositions of the present disclosure applicable as an intervention to a wide variety of pathological conditions. The potassium osmolytes of the present disclosure are easy-to-administer and are also easily stored, contributing to the overall inexpensiveness and availability of the therapeutic compositions of the instant disclosure to patients. By specifically targeting electrical signal pathways as a means of changing cell phenotype and ultimately treating pathological conditions, the therapeutic compositions of the present disclosure are also combinable with other interventions, e.g., chemical-based treatments, enabling multi-pronged treatment approaches.

Although the disclosed subject matter has been described and illustrated with respect to embodiments thereof, it should be understood by those skilled in the art that features of the disclosed embodiments can be combined, rearranged, etc., to produce additional embodiments within the scope of the invention, and that various other changes, omissions, and additions may be made therein and thereto, without parting from the spirit and scope of the present invention.

What is claimed is:

1. A method of treating a patient comprising:
    identifying inflammation of a joint of the patient; and
    administering to the intra-articular region of the joint an amount of a therapeutic composition, the therapeutic composition includes a hyperosmolar $K^+$ solution including:
        potassium gluconate, potassium aspartate, or combinations thereof,
    wherein the therapeutic composition is administered via injection, oral administration, topical administration, inhalation, or combinations thereof.

2. The method according to claim 1, wherein the concentration of the potassium gluconate, potassium aspartate, or combinations thereof in the intra-articular space is made to be above about 2 mM.

3. The method according to claim 2, wherein the concentration of the potassium gluconate, potassium aspartate, or combinations thereof in the intra-articular space is made to be above about 40 mM.

4. The method according to claim 1, wherein the inflammation of the joint is caused by osteoarthritis, rheumatoid arthritis, surgery at or proximate to the joint, or combinations thereof.

5. The method according to claim 1, wherein identifying inflammation of the joint of the patent includes:

identifying increased activation, in or proximate to the intra-articular region, of chondrocytes, macrophages, or combinations thereof.

* * * * *